May 11, 1965 W. ROBERTS Plant Pat. 2,509
GLADIOLUS PLANT
Filed Nov. 6, 1963
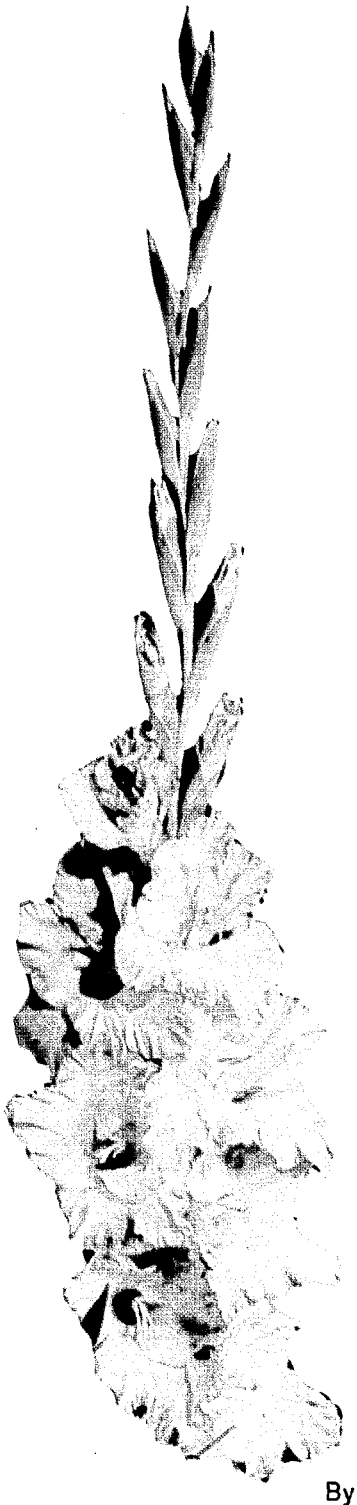
INVENTOR
Winston Roberts
By Lamont Johnston
ATTORNEY United States Patent Office Plant Pat. 2,509
Patented May 11, 1965

2,509
GLADIOLUS PLANT

Winston Roberts, Boise, Idaho, assignor to Selected Glads, Inc., New Albany, Ind., a corporation of Tennessee Filed Nov. 6, 1963, Ser. No. 321,986
1 Claim. (Cl. Plt.—85)

My present invention relates to a new and improved variety of gladiolus plant and is notable particularly for its rugged vigor, ruffles, florescence and pure color. In my breeding work I strived for health and purity of color, and have identified this variety as seedling No. 1759–3.

To the best of my knowledge, this new variety is the result of a cross between the variety Celestial Rose and an unnamed seedling whose parents were Columbia and Bermuda (all unpatented), Celestial Rose being the seed parent and the seedling the pollen parent. Hand cross pollination was done by me in my field at Boise, Idaho, but no precaution was taken to prevent admixture of other varieties by bees or insects, except that stigma and pistil were pinned to upper petal by toothpicks when the cross was made.

The new variety has been asexually reproduced by me in Idaho by natural increase from cormels through several generations and its characteristics have proven to be permanently fixed.

The illustration, made a part of this application, shows a single bloom spike of this variety, reduced in size, and is as nearly true to color as it is possible to depict. The illustration shows the intense ruffling and the combination of a light, pure pink, color with a creamy-white throat.

In the following detailed description, color plate references are to the "Horticultural Colour Chart," by the British Colour Council. Where there are other references to color, the ordinary dictionary meanings of the terms are intended.

*The plant*

Growth: Extremely vigorous, bloom spike averaging about 60 inches in height. Excellent propagator.

Blooming: The variety is a mid-season bloomer, coming into bloom in 85 to 90 days from large bulbs in the North.

Stems: Straight and willowy. Diameter of cutting stem at base is ⅜ inch. Color of stem at base of plant is a light rose-purple.

Foliage: Healthy green; it has quite wide leaves, 1¾ in. across. Plant foliage, excluding the flower spike, averages about 34 to 36 inches in height. Upper leaves of plant are upright; lower leaves droop.

Corms: Husk is straw colored and does not cling to the bulbs; very papery. Flesh is Straw Yellow $604/_2$.

*The flower*

Spike: Flowerhead is 24 to 26 inches with nineteen to twenty-one buds with seven to nine open at one time.

Bud:

*Size.*—Opening bud is 3¼ inches long.

*Opening.*—Five to six show color at one time.

Flower:

*Arrangement.*—The flowers usually are formally placed, or double-row placement and usually all face forward on the stem.

*Size.*—Individual florets measure 5 to 5¼ inches in diameter. Upper blooms are progressively smaller.

*Forms.*—The florets are round, quite flat open and heavily ruffled.

*Keeping qualities.*—Keeps and opens well.

Petals:

*Shape.*—Round and intensely ruffled.

*Size.*—Outer petals 2½ inches across; lip petal, 1½ inches across.

*Aspect.*—Substance is extremely heavy. The surface is glistening with some creasing; intensely ruffled.

*Fragrance.*—None.

*Color.*—Dawn Pink $523/_2$. Edges are $523/_1$ shading to $523/_3$ in the hearts of the flowers. Blotch and mid-ribs are white. General effect of the color is deeper on the reverse than on the front of the flower.

Reproductive organs:

*Stamens.*—Purple.

*Pistil.*—Deep rose.

*Comparisons*

My new variety resembles Coronation (unpatented) more than any other variety, but differs from it principally as follows:

(1) My variety is a somewhat lighter and cooler shade of pink.

(2) My variety has heavier substance and more waxy texture.

(3) My variety is more ruffled.

(4) My variety grows taller.

(5) My variety produces more bulblets.

(6) My variety grows better from bulblets.

(7) My variety has more buds and opens more florets at one time.

Having thus disclosed my invention, I claim:

The new and distinct variety of gladiolus plant, substantially as herein shown and described, characterized by its beautiful color and texture of blossoms, rugged growth and intense ruffling.

No references cited.

ABRAHAM G. STONE, *Primary Examiner.*